(12) United States Patent
Lenglet et al.

(10) Patent No.: US 6,875,338 B2
(45) Date of Patent: Apr. 5, 2005

(54) PROCESS FOR ENDOTHERMIC CONVERSION OF HYDROCARBONS, ITS USES, AND A UNIT FOR CARRYING OUT THE PROCESS

(75) Inventors: Eric Lenglet, Rueil Malmaison (FR); Frédéric Hoffmann, Sainte Foy les Lyon (FR); Nicolas Boudet, Lyons (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 429 days.

(21) Appl. No.: 09/984,372

(22) Filed: Oct. 30, 2001

(65) Prior Publication Data

US 2002/0052534 A1 May 2, 2002

(30) Foreign Application Priority Data

Oct. 31, 2000 (FR) .............................................. 00 14019

(51) Int. Cl.[7] .......................... C10G 59/02; C07C 2/54; C07C 5/32
(52) U.S. Cl. ............................. 208/62; 208/63; 208/64; 585/323; 585/911; 585/912
(58) Field of Search .............................. 208/62, 63, 64; 585/323, 911, 912

(56) References Cited

U.S. PATENT DOCUMENTS

| 2,271,646 | A | | 2/1942 | Kassel | |
|---|---|---|---|---|---|
| 3,326,996 | A | * | 6/1967 | Henry et al. | ................. 585/402 |
| 5,885,439 | A | * | 3/1999 | Glover | ......................... 208/64 |

* cited by examiner

*Primary Examiner*—Walter D. Griffin
(74) *Attorney, Agent, or Firm*—Millen, White, Zelano & Branigan, P.C.

(57) ABSTRACT

The invention concerns a process for converting hydrocarbons using at least one globally endothermic chemical reaction, in which a hydrocarbon feed successively traverses at least two reaction zones each containing at least one solid catalyst and comprising between said reaction zones an intermediate step, in a non catalytic zone, for reheating the stream (ST) from the first of the two reaction zones prior to its introduction into said second reaction zone, and in which said reheating is carried out in a heat exchanger, with heat transfer essentially by convection using a thermal fluid TF with a coking sensitivity index CS that is less than that of the stream ST, the difference in temperature $\Delta T$ between the temperature of the fluid TF at the inlet to the exchanger and the temperature of the stream ST at the heat exchanger outlet being less than 250° C. The invention also concerns the use of said process for converting hydrocarbons and a unit for carrying out the process.

30 Claims, 3 Drawing Sheets

PROCESS FOR ENDOTHERMIC CONVERSION OF HYDROCARBONS, ITS USES, AND A UNIT FOR CARRYING OUT THE PROCESS

The petroleum and petrochemicals industry employs many processes for converting hydrocarbons by means of endothermic chemical reactions. Particular reactions are cracking reactions, dehydrogenation reactions and hydrocarbon reforming reactions.

Such reactions require means for heating the feed to high temperatures to supply the energy required for the reaction. In many cases, heating the feed is sufficient to reach the desired temperature, and to provide the energy necessary for reaction.

In other cases, the cooling caused by endothermic reactions is such that it is not possible to carry out the chemical reaction in a single reactor. This is particularly the case for catalytic hydrocarbon reforming, or for producing high octane number gasoline.

The feed, typically a naphtha, with added hydrogen, successively traverses a number of catalytic beds, with reheating between each bed to compensate for the drop in temperature in those catalytic beds due to the endothermicity of the reaction. Usually, several reactors are used, each containing at least one bed of solid catalyst or, in equivalent manner, catalytic zones of catalyst deposited on at least a portion of the solid surfaces of those zones.

The feed is reheated in radiative pipe furnace, where the feed circulates in coils heated in the radiation zone supplied by burners. A process for dehydrogenation of light paraffins, for example propane, is known for the production of propylene, where the feed successively traverses a plurality of reactors each containing at least one bed of catalyst, with intermediate reheating between each reactor in the radiative pipe furnace.

Typically, such conversion processes produce unsaturated compounds that promote coke formation and in particular participate in catalytic coking. Catalytic coking particularly occurs in the pipe furnace; the feed that typically circulates in the furnace at temperatures of about 500° C. or 600° C. is subjected to the radiation from the burners, where the combustion gases are typically at a temperature in the range 1100° C. to 1600° C., and transmit high heat flows, for example of the order of 50 kW/m2 or more.

Such undesirable coking reactions in the reheating furnace are also associated with undesirable thermal cracking reactions. This results in a reduction in the reaction yields and the unit has to be stopped to decoke the furnace.

Chemical reactors are also known for endothermic reactions, in particular that described in U.S. Pat. 5,600,053 where heat is supplied in a manner that is less severe than furnace, and carried out in the reactor in the catalytic bed. These reactors, or reactor-exchangers, heat the catalytic bed itself by dint of exchange surfaces immersed in the catalytic bed heated by a heat carrying fluid. In that second type of chemical reactor, heating is less severe than in a furnace, but generates "hot spots" in the catalyst where it comes into contact with the heating surfaces. In many cases, this leads to local deactivation of the catalyst, which has a relatively narrow service temperature range.

Thus, that second type of reactor and the conversion has disadvantages as regards catalyst use.

The invention aims to provide a process and a unit for converting hydrocarbons by endothermic reactions, which removes or substantially limits catalytic coking, which occurs in the event of coke promoting reactants, and not exhibiting problems with the use of the catalyst, in particular not causing hot spots in the catalyst.

The invention also aims to provide a process for converting hydrocarbons by endothermic reactions, comprising integration and high energy efficiency.

In particular, the invention aims to provide a process for dehydrogenating hydrocarbons with a high conversion yield, for the production of olefins. An important use of the olefinic feed formed concerns the alkylation of aromatic compounds and in particular the production of alkylbenzenes (often used as a starting material for the production of detergent bases).

The process of the present invention can be defined as a process for converting hydrocarbons using at least one globally endothermic chemical reaction, in which a hydrocarbon feed successively traverses at least two reaction zones each containing at least one solid catalyst and comprising between said reaction zones an intermediate step, in a non catalytic zone, for reheating the stream (ST) issued from the first of the two reaction zones prior to its introduction into said second reaction zone, and in which said re-heating is carried out in a heat exchanger, with heat transfer essentially by convection using a thermal fluid TF with a coking sensitivity index CS that is less than that of the stream ST, the difference in temperature ΔT between the temperature of the fluid TF at the inlet to the exchanger and the temperature of the stream ST at the heat exchanger outlet being less than 250° C., preferably less than 200° C.

In accordance with the invention, the partially converted stream of feed issuing, for example, from the first catalytic bed reactor, is reheated essentially by convection and not principally by radiation, i.e., using much less severe heating means than used in a radiative reheating furnace; the difference in temperature ΔT between the hot thermal fluid TF at the exchanger inlet and the stream ST at the outlet from the heat exchanger is less than about 250° C., preferably less than 200° C., and usually in the range 10° C. to 150° C., limits included, preferably in the range 10° C. to 120° C., included.

This temperature difference between the fluids is much more moderate than in a furnace where the combustion gases are typically at temperatures of more than 1100° C., and thus normally more than 500° C. higher than the temperature of the stream ST from the process that is heated in the furnace.

In accordance with the invention, the risks of coking and reactant degradation are considerably limited. Further, this "mild" reheating of the reactants is carried out on the fluid alone leaving one reaction zone, in the absence of a catalyst. Thus, the risk of producing hot spots in the catalyst, which are encountered in catalytic reactor-exchangers, is avoided.

In the present invention, a thermal fluid TF is normally selected that is a relatively low coke promoter, which can thus be readily heated in a furnace. Thus, the relatively severe heating effect is transferred to the thermal fluid and no longer to the reaction feed.

The coking sensitivity index CS is conventionally defined for the fluids TF and ST by the relationship:

$$CS = i + 3 \times j$$

where:

i is the percentage by weight of the monoolefinic compounds in the fluid; and j is the percentage by weight of polyunsaturated compounds in the fluid, said polyunsaturated compounds containing at least two olefinic bonds.

As an example, for a fluid containing 10% by weight of monoolefinic compounds, and no polyunsaturated compounds containing at least two olefinic bonds, CS is equal to 10.

To implement the present invention, non coking thermal fluids are usually used, such as a fluid selected from the group formed by steam, molten salts and molten metals, for which the index CS is zero, or a mixture of at least two of said fluids.

In the process of the present invention, the thermal fluid TF is usually a fluid selected from the group formed by gaseous thermal fluids, that can transfer heat by sensible heat alone.

Usually, the thermal fluid is steam, under pressure and superheated under conditions such that there is no condensation, even partial condensation, of said steam. This steam is typically at a temperature of more than about 400° C. at the inlet such that at the outlet from the heat exchanger it is used as a gaseous fluid vector for sensible heat and not for latent heat. Its pressure is normally about 0.1 to about 15 MPa.

It is also possible to use a stream that is rich in hydrogen, a stream of recycle gas that is usually rich in hydrogen and comprises limited quantities of light hydrocarbons, possibly after hydrogenation of the unsaturated compounds it contains, for example by catalytic means. The scope of the present invention also encompasses using all or a portion of the feed itself as the thermal fluid, unconverted, circulating upstream of the first reaction zone and possibly with added recycle gas.

Thermal fluids containing substantial quantities of olefins, diolefins, and to a lesser extent aromatic compounds are to be avoided as those chemical compounds are known to the skilled person to be coke promoters.

Normally, a thermal fluid TF is selected with a CS index of 100 or less, usually with a CS index of 50 or less, preferably with a CS index of 10 or less.

The thermal fluid TF is usually an inorganic liquid stream selected from the group formed by molten metals and molten salts. In a typical implementation, the temperature difference $\Delta T$ is in the range 10° C. to 150° C., limits included, preferably in the range 10° C. to 120° C., limits included.

Usually, the thermal fluid TF is a stream of steam at a pressure of about 0.7 MPa absolute or more, at least a portion of said stream TF at the outlet from the heat exchanger being depressurised in a turbine to generate power, in particular electrical power. In a particular implementation, said turbine drives a compressor for recycling hydrogen-rich gas, this gas being added to the hydrocarbons to carry out the chemical reaction under hydrogen pressure.

The process of the present invention can be employed to dehydrogenate hydrocarbons selected from the group formed by ethane, propane, normal-butane, isobutane, paraffins containing 5 to 20 carbon atoms per molecule, mono-olefinic compounds comprising 4 to 20 carbon atoms per molecule and ethylbenzene.

In particular, this process is used to dehydrogenate a feed of long chain paraffins essentially containing 10 to 14 carbon atoms per molecule, limits included, to produce a benzene alkylation feed, in which the paraffin feed traverses at least two reaction zones in the presence of a dehydrogenation catalyst, with intermediate reheating in a heat exchanger, to obtain a paraffin conversion of about 15% to 50% by weight. Within the context of this use for the production of a benzene alkylation feed, the number of reaction zones is preferably in the range 2 to 6, the temperatures of these zones are generally in the range 440° C. to 520° C. and the mole ratio of hydrogen with respect to the hydrocarbons in these zones is generally in the range 1:1 to 15:1.

A further frequent use of the process of the invention is reforming hydrocarbons in hydrogen.

In a particular implementation of the process of the invention, the stream of thermal fluid TF is composed of steam at a pressure of about 1.5 MPa to about 13 MPa absolute, and at least a portion of this stream TF is used, at the exchanger outlet, in condensation, to reboil a fractionation distillation column.

When employing the process of the invention in a reaction for alkylation of olefins produced by paraffin dehydrogenation using benzene, in the presence of excess benzene, a step is provided for fractionating the effluent from the alkylation step in a distillation column to separate excess benzene from less volatile compounds comprising non transformed paraffins and alkylbenzenes, in which at least a portion of stream TF from the outlet from said exchanger is used to reboil said distillation column.

The present invention also concerns a unit for carrying out the process described above in which the exchanger used is a plate heat exchanger, in particular a plate heat exchanger with stainless steel plates.

In a particular implementation, the process of the present invention employs a thermal fluid TF that is a stream of steam at a pressure P1 wherein a portion is recompressed downstream of the heat exchanger, by a steam ejector supplied with a stream of steam at a pressure P2 that is higher than P1, to be recycled at least in part upstream of said exchanger.

DETAILED DESCRIPTION OF THE DRAWINGS

Figure 1:
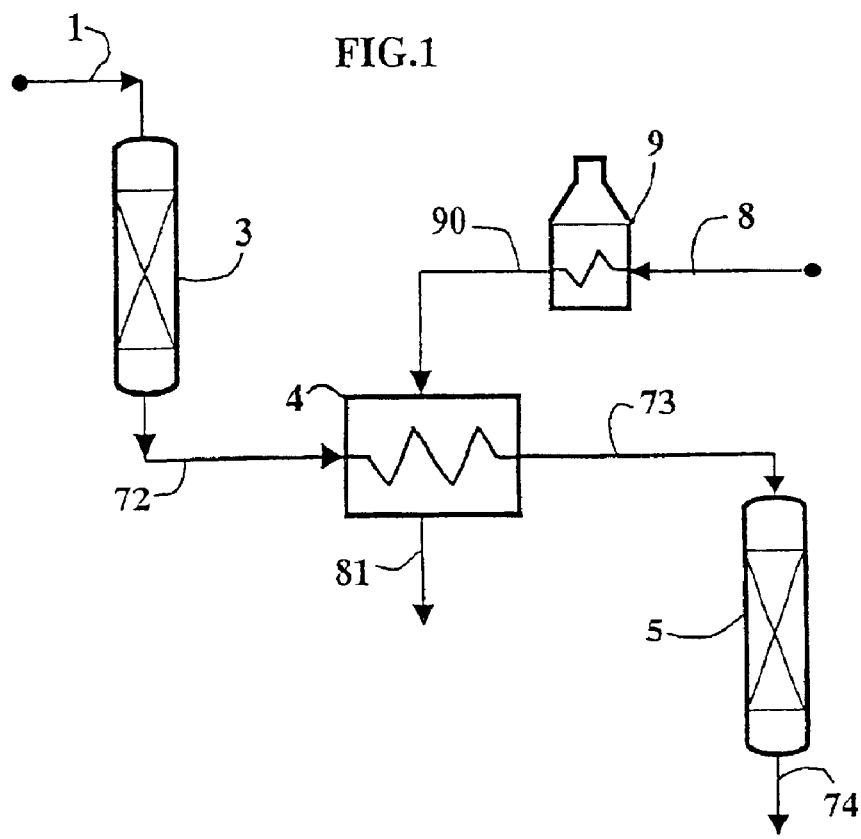
FIG. 1 shows part of a unit for converting hydrocarbons to carry out the process of the invention.

Referring now to FIG. 1, a preheated stream circulating in line (1) and containing a hydrocarbon feed traverses a first bed of catalyst in a reactor (3), which produces a stream ST containing the partially converted feed sent via line (72) to a heat exchanger (4). The reaction is endothermic, so the temperature of the stream ST circulating in line (72) at the outlet from reactor (3) is lower than that of the stream entering the reactor (3) via line (1). This stream ST is heated by indirect heat exchange, essentially by convection, in the heat exchanger (4), to raise its temperature to a sufficient level. The reheated stream ST is sent via line (73) to a reactor (5) containing a bed of catalyst to obtain supplemental conversion of the feed from reactor (3). The product from reactor (5) is recovered via line (74). A stream essentially comprising relatively low coking or non coking chemical compounds is sent via line (8) then heated in a pipe furnace (9). It then supplies heat exchanger (4), via line (90) as thermal fluid TF and leaves this exchanger via line (81). The difference in temperature $\Delta T$ between the temperature of this fluid TF in line (90) at its inlet to exchanger (4) and the temperature of the fluid ST circulating in line (73) at the outlet from exchanger (4) is selected so as to be relatively low, for example 10° C. to 100° C., so as to substantially eliminate the risks of coking in exchanger (4).

Figure 2:
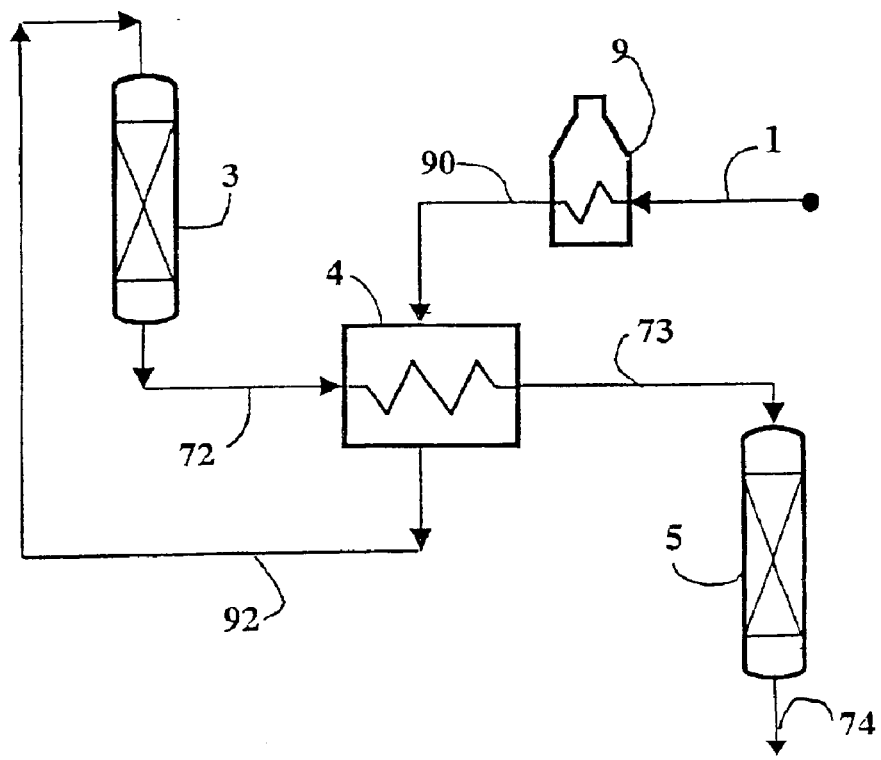
FIG. 2 shows part of a unit for converting hydrocarbons to carry out a first variation of the process of the invention.

Reference should now be made to FIG. 2, which uses the same reference numerals as those employed for FIG. 1.

In this variation of the invention, a stream circulating in line (1) and containing the feed, or, for example a hydrocarbon feed with added hydrogen-rich recycle gas that constitutes the hot thermal fluid TF, after heating in furnace (9). Stream TF is sent to exchanger (4) via line (90). At the outlet from exchanger (4), it then supplies the first reactor (3) via line (92). The remainder of the unit is identical to that described in relation to FIG. 1.

FIGS. 1 and 2, show only two catalytic stages; in practice, it is possible to employ a larger number of reactors or catalytic zones, for example 3 to 10 catalytic zones, with intermediate reheating. At least a portion of these reheating steps is carried out in accordance with the invention.

The catalytic beds are of the solid catalyst type. The catalyst particle size and the geometry of the catalytic beds (radial, axial or the like) do not limit the invention, which can be implemented with all types of catalytic beds: fixed bed, moving bed, fluid bed, or catalyst deposited on the surface of solids (thin layers), for example monolithic reactors.

Figure 3:
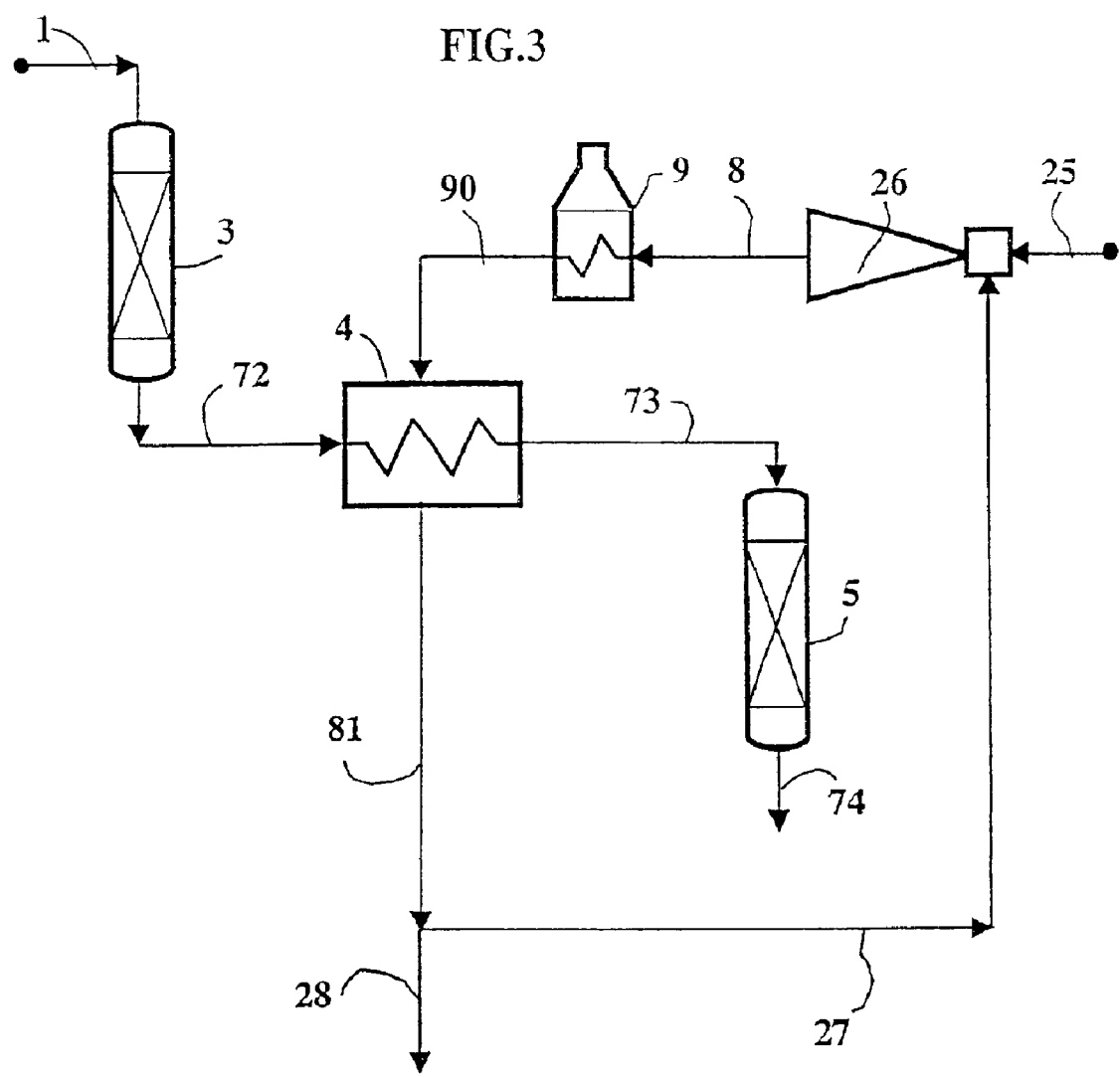
FIG. 3 shows part of a unit for converting hydrocarbons to carry out a second variation of the process of the invention.

Reference should now be made to FIG. 3, using the same reference numerals as those employed for FIG. 1.

A portion of the unit of FIG. 3 is identical to that of FIG. 1; in FIG. 3, the thermal fluid TF is constituted by steam, for example medium pressure steam P1 (1 to 2.5 MPa, for example); at the outlet from exchanger (4), a portion of the thermal fluid TF is purged via line (28) (used for other heating needs, or to generate mechanical or electrical power; these means are not shown); a further portion of stream TF is sent via line (27) then recompressed in stream ejector (26) supplied by high pressure steam entering said ejector via line (25), for example at a pressure P2 in the range 10 to 13 MPa absolute.

At the outlet from ejector (26), the steam stream is sent via line (8) and heated in furnace (9) to constitute the hot thermal fluid TF sent to heat exchanger (4) via line (90).

Figure 4:
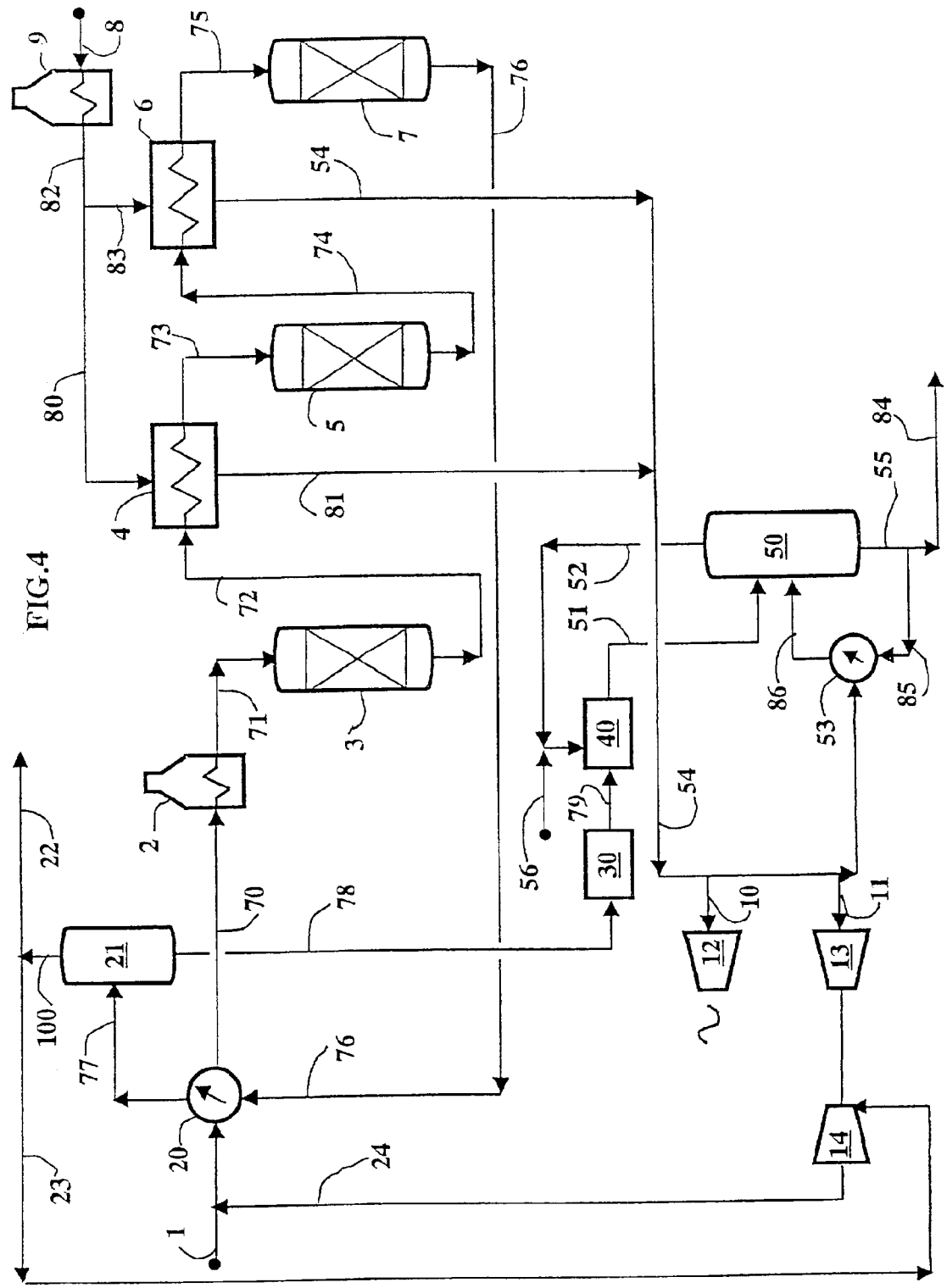
FIG. 4 shows part of a chemical complex for the production of alkylbenzenes, comprising a long chain paraffin dehydrogenation step in accordance with the process of the invention.

Reference should now be made to FIG. 4. This figure shows a portion of a petrochemicals complex for the production of alkylbenzenes, in particular that known as linear alkyl benzene LAB.

The stream circulating in line (1) that is rich in feed hydrocarbons, essentially paraffins, in particular linear paraffins containing 10 to 14 carbon atoms, and supplemented by a stream of hydrogen-rich recycle gas arriving via line (24) is preheated in exchanger (20), heated to higher than the reaction temperature, for example 485° C., in furnace (2) arriving via line (70), before supplying the first catalytic dehydrogenation reactor (3) via line (71). At the outlet from reactor (3), stream ST containing the partially converted feed is sent via line (72) then reheated in accordance with the invention in heat exchanger (4). It then supplies the second catalytic dehydrogenation reactor (5) via line (73). At the reactor outlet (5), the reaction fluid formed is sent via line (74) then reheated in heat exchanger (6) (also in accordance with the invention) before being sent to the third catalytic bed dehydrogenation reactor (7) via line (75).

At the outlet from reactor (7), the effluent from the catalytic dehydrogenation section is sent to exchanger (20) via line (76) then from the outlet from this exchanger, it is sent to a gas/liquid drum separator (21) via line (77). The gas produced in drum (21) leaves said drum via line (100) and is then separated into an excess of hydrogen-rich gas evacuated via line (22), and into a stream of recycle gas sent via line (23) then recompressed by compressor (14) to constitute the stream sent via line (24) to line (1) for arrival of the feed to form the feed-recycle gas mixture mentioned above.

The thermal fluid circuit is constituted by a stream of steam arriving via line (8) (for example at 40 bars absolute in the heat exchangers of the invention). This stream of steam is heated in the radiative pipe furnace (9), to constitute a thermal fluid TF that can supply heat exchangers (4) and (6) respectively via lines (80) and (83).

Downstream of heat exchanger (4) and (6), the partially cooled thermal fluid TF (medium pressure steam) supplies three distinct networks:

The fluid sent to the first network, respectively via lines (81) and (54), supplied via line (10) is depressurised in a turbine (12) for the production of electrical energy;

The fluid sent to the second network via line (11) is depressurised in turbine (13) to drive the recycle gas compressor (14);

The fluid sent to the third network via line (54) supplies and acts as the thermal fluid for the condensation reboiler (53) of a distillation column (50). This column (50) is supplied with the stream of liquid effluent from the dehydrogenation section, from drum separator (21) via line (78); this liquid stream from drum (21) successively traverses a selective hydrogenation unit (for diolefins) (30), then a benzene alkylation unit (40) via line (79). This unit is supplied with benzene via line (56), supplemented with benzene recycled via line (52). Column (50) is the first fractionation column for effluent from the alkylation unit (40) and is supplied via line (51). This column (50) carries out fractionation of the excess benzene (stream recycled via line (52)) of less volatile products in particular containing untransformed paraffins and alkylbenzenes evacuated via line (84). This column (50) comprises a reboiler (53) supplied via line (85) the reheated effluent from which is returned to column (50) via line (86).

This scheme performs well on the energetic level as the thermal fluid TF used for intermediate reheating of the dehydrogenation section is also used in an integrated manner in the complex downstream of these exchangers for the production of electrical energy and/or mechanical energy and/or heat energy.

The catalytic beds are, for example (although this does not limit the invention), radial catalytic beds containing dehydrogenation catalyst, for example of the platinum/tin on an alumina support type, in the form of beads. The temperatures at the inlet to the catalytic beds can typically be of the order of 420° C. to 550° C., preferably 450° C. to 500° C.

The mole ratio of hydrogen with respect to the hydrocarbons is typically in the range 1 to 15, preferably in the range 2 to 10, and the pressure at the outlet from the last reactor is typically in the range 0.10 MPa (megapascals) to 5 MPa absolute, limits included, and preferably in the range 0.15 MPa to 0.5 MPa absolute, limits included.

The space velocities (HSV, hourly space velocity) can typically be between $10h^{-1}$ and $250\ h^{-1}$ for each catalytic bed.

The unit can optionally comprise not only 3 catalytic zones, as indicated in the diagram in FIG. 4, but 4 or 5 catalytic zones, for example, with intermediate reheating, or more if necessary.

Depending on the temperatures used, such a unit can reach very high degrees of conversion, for example in the range 15% to 50%, in particular in the range 18% to 25% by weight of the paraffin feed employed, without notable risks of coking, and with no hot spots in the catalyst.

What is claimed is:

1. A process for converting hydrocarbons using at least one globally endothermic chemical reaction, comprising:
    successively traversing a hydrocarbon feed through at least two reaction zones, each containing at least one solid catalyst and an intermediate reheating step, in a non catalytic zone, for reheating the stream (ST) from the first of the two reaction zones prior to its introduction into said second reaction zone, wherein said reheating step is between said reaction zones wherein said reheating is carried out in a heat exchanger, in which heat transfer is performed essentially by convection using a thermal fluid TF with a coking sensitivity index CS that is less than that of the stream ST, and heating said thermal fluid TF in a furnace upstream of the heat exchanger, and wherein the difference in temperature $\Delta T$ between the temperature of the thermal fluid TF at the inlet to the exchanger and the temperature of the stream ST at the heat exchanger outlet is less than 250° C., and said thermal fluid TF is selected from:
  a hydrogen-rich gaseous stream,
  a stream of recycle gas, and
  a gaseous stream containing hydrocarbons from the feed circulating upstream of the first reaction zone.

2. A process according to claim 1, in which $\Delta T$ is in the range of 10° C. to 150° C., limits included.

3. A process according to claim 1, wherein said hydrocarbon feed comprises hydrocarbons selected from the group consisting of ethane, propane, normal-butane, isobutane, paraffins containing 5–20 carbon atoms per molecule, mono-olefinic compounds comprising 4 to 20 carbon atoms per molecule, ethylbenzene, and mixtures of at least two of these hydrocarbons, and wherein said hydrocarbons are subjected to dehydrogenation in said at least two reaction zones.

4. A process according to claim 3, wherein said hydrogen feed comprises long chain paraffins essentially containing 10–14 carbon atoms per molecule, wherein the paraffin feed traverses said at least two reaction zones in the presence of a dehydrogenation catalyst, with intermediate reheating in said heat exchanger, to obtain a paraffin conversion of about 15%–50% by weight.

5. A process according to claim 4, wherein said hydrocarbon feed traverses 2–6 reaction zones having temperature of 440° C.–520° C. and wherein the mole ratio of hydrogen with respect to the hydrocarbons in these zones is 1:1 to 15:1.

6. A process according to claim 4, further comprising
  alkylating olefins produced by the paraffin dehydrogenation, in the presence of excess benzene,
  fractionating the effluent from the alkylation step in a distillation column to separate excess benzene from less volatile compounds comprising non transformed paraffins and alkylbenzenes, and
  using at least a portion of thermal fluid TF from the outlet from said exchanger reboil fluid in said distillation column.

7. A process according to claim 1, for reforming hydrocarbons in hydrogen.

8. A process according to claim 1, wherein each of said least two reaction zones is a reactor containing at least one solid catalyst and said heat exchanger is a plate heat exchanger.

9. A process according to claim 1, wherein said heat exchanger is a plate heat exchanger comprising stainless steel plates.

10. A process for converting hydrocarbons using at least one globally endothermic chemical reaction, comprising:
  successively traversing a hydrocarbon feed through at least two reaction zones, each containing at least one solid catalyst and an intermediate reheating step, in a non catalytic zone, for reheating the stream (ST) from the first of the two reaction zones prior to its introduction into said second reaction zone, wherein said reheating stop is between said reaction zones wherein said reheating is carried out in heat exchanger, in which heat transfer is performed essentially by convection using a thermal fluid TF with a coking sensitivity index CS that is less than that of the stream ST, and heating said thermal fluid TF in a furnace upstream of the heat exchanger, and wherein the difference in temperature $\Delta T$ between the temperature of the thermal fluid TF at the inlet to the exchanger and the temperature of the stream ST at the heat exchanger outlet is less than 250° C., and said thermal fluid TF comprises a stream of steam at a pressure of 0.7 MPa absolute or more, at least a portion of said thermal fluid TF at the outlet from the heat exchanger being depressurised in a turbine to generate power.

11. A process according to claim 10, in which said turbine drives a compressor for recycling a hydrogen-rich gas, this gas being added to hydrocarbons to carry out the chemical reaction under hydrogen pressure.

12. A process according to claim 10, in which the thermal fluid TF comprises a stream of steam at a pressure P1, and downstream of the heat exchanger a steam ejector supplied with a stream at a pressure P2 that is higher than P1, to be recycled at least in part upstream of said exchanger.

13. A process according to claim 12, wherein said plate heat exchanger comprises stainless steel plates.

14. A process according to claim 10, wherein said power is electrical power.

15. A process according to claim 10 wherein the thermal fluid TF comprises a stream of steam at a pressure P1, and further comprising downstream of the heat exchanger increasing the pressure of said stream of steam to a pressure P2 that is higher than P1, and recycling at least part of the increased pressure stream to a point upstream of said heat exchanger into said furnace.

16. A process according to claims 10, in which $\Delta T$ is in the range of 10° C. to 150° C., limits included.

17. A process according to claim 10, wherein said hydrocarbon feed comprises hydrocarbons selected from the group consisting of ethane, propane, normal-butane, isobutane, paraffins containing 5–20 carbon atoms per molecule, mono-olefinic compounds comprising 4 to 20 carbon atoms per molecule, ethylbenzene, and mixtures of at least two of these hydrocarbons, and wherein said hydrocarbons are subjected to dehydrogenation in said at least two reaction zones.

18. A process according to claim 17, wherein said hydrocarbon feed comprises long chain paraffins essentially containing 10–14 carbon atoms per molecule, wherein the paraffin feed traverses said at least two reaction zones in the presence of a dehydrogenation catalyst, with intermediate reheating in said heat exchanger, to obtain a paraffin conversion of about 15%–50% by weight.

19. A process according to claim 18, wherein said hydrocarbon feed traverses 2–6 reaction zones having temperature of 440° C. 520° C. and wherein the mole ratio of hydrogen with respect to the hydrocarbons in these zones is 1:1 to 15:1.

20. A process according to claim 18, further comprising
  alkylating olefins produced by the paraffin dehydrogenation, in the presence of excess benzene
  fractionating the effluent from the alkylation step in a distillation column to separate excess benzene from less volatile compounds comprising non transformed paraffins and alkylbenzenes, and
  using at least a portion of thermal fluid TF from the outlet from said exchanger reboil fluid in said distillation column.

21. A process according to claim 10, for reforming hydrocarbons in hydrogen.

22. A process according to claim 10, wherein said hydrocarbon feed is subjected to hydrocarbon conversion in said at least two reaction zones, under hydrogen pressure, and said turbine drives a compressor for recycling hydrogen-rich gas to said reaction zones.

23. A process for converting hydrocarbons using at least one globally endothermic chemical reaction, comprising:

successively traversing a hydrocarbons feed through at least two reaction zones, each containing at least one solid catalyst at and an intermediate reheating step, in a non catalytic zone, for reheating from the stream (ST) from the two reaction zones prior to its introduction into said second reaction zone, wherein said reheating step is between said reaction zones wherein said reheating is carried out in a heat exchanger, in which heat transfer is performed essentially by convection using a thermal fluid TF with a coking sensitivity index CS that is less than that of the stream ST, and heating said thermal fluid TF in a furnace upstream of the heat exchanger, and wherein the difference in temperature ΔT between the temperature of the thermal fluid TF at the inlet to the exchanger and the temperature of the stream ST at the heat exchanger outlet is less than 250° C., and wherein said thermal fluid TF is composed of steam at a pressure of about 1.5 MPa to about 13 MPa absolute, and at least a portion of said thermal fluid TF is used, at the exchanger outlet, in condensation, to rebel a fluid in a fractional distillation column.

24. A process according to claim 23, wherein said hydrocarbon feed comprises hydrocarbons selected from the group consisting of ethane, propane, normal-butane, isobutane, paraffins containing 5–20 carbon atoms per molecule, mono-olefinic compounds comprising 4 to 20 carbon atoms per molecule, ethylbenzene, and mixtures of at least two of these hydrocarbons, and wherein said hydrocarbons are subjected to dehydrogenation in said at least two reaction zones.

25. A process according to claim 23, wherein said hydrocarbon feed comprises long chain paraffins essentially containing 10–14 carbon atoms per molecule, wherein the paraffin feed traverses said at least two reaction zones in the presence of a dehydrogenation catalyst, with intermediate reheating in said heat exchanger, to obtain a paraffin conversion of about 15%–50% by weight.

26. A process according to claim 25, wherein said hydrocarbon feed traverses 2–6 reaction zones having temperature of 440° C.–520° C. and wherein the mole ratio of hydrogen with respect to the hydrocarbons in these zones is 1:1 to 15:1.

27. A process according to claim 25, further comprising alkylating olefins produced by the paraffin dehydrogenation, in the presence of excess benzene, fractionating the effluent from the alkylation step in a distillation column to separate excess benzene from less volatile compounds comprising non transformed paraffins and alkylbenzenes, and using at least a portion of thermal fluid TF from the outlet from said exchanger reboil fluid in said distillation column.

28. A process for converting hydrocarbons using at least one globally endothermic chemical reaction, comprising:

successively traversing a hydrocarbon feed through at least two reaction zones, each containing at least one solid catalyst and an intermediate reheating step, in a non catalytic zone, for reheating the stream (ST) from the first of the two reaction zones prior to its introduction into said second reaction zone, wherein said reheating step is between said reaction zones wherein said reheating is carried out in a heat exchanger, in which heat transfer is performed essentially by convection using a thermal fluid TF with a coking sensitivity index CS that is less than that of the stream ST, and heating said thermal fluid TF in a furnace upstream of the heat exchanger, and wherein the difference in temperature ΔT between the temperature of the thermal fluid TF at the inlet to the exchanger and the temperature of the stream ST at the heat exchanger outlet is less than 250° C., and said thermal fluid TF is selected from:
a hydrogen-rich gaseous stream,
a stream of recycle gas, and
a gaseous stream containing hydrocarbons from the feed circulating upstream of the first reaction zone; or said thermal fluid TF comprises an inorganic liquid stream selected from molten metals and molten salts; or said thermal fluid TF comprises a stream of steam at a pressure of 0.7 MPa absolute or more, and at least a portion of said thermal fluid TF at the outlet from the heat exchanger being depressurised in a turbine to generate power; or said thermal fluid TF is comprises steam at a pressure of 1.5 MPa to 13 MPa absolute, and at least a portion of said thermal fluid TF is used, at the exchanger outlet, in condensation, to reboil a fluid in a fractional distillation column.

29. A process according to claim 28, in which the thermal fluid TF comprises an inorganic liquid stream selected from the group consisting of molten metals and molten salts.

30. A processes for converting hydrocarbons using at least one globally endothermic chemical reaction, comprising:

successively traversing a hydrocarbon feed through at least two reaction zones, each containing at least one solid catalyst and an intermediate reheating step, in a non catalytic zone, for reheating the stream (ST) from the first of the two reaction zones prior to its introduction into said second reaction zone, wherein said reheating step is between said reaction zones wherein said reheating is carried out in a heat exchanger, in which heat transfer is performed essentially by convection using a thermal fluid TF with a coking sensitivity index CS that is less than that of the stream ST, and heating said thermal fluid TF in a furnace upstream of the heat exchanger, and wherein the difference in temperature ΔT between the temperature of the thermal fluid TF at the inlet to the exchanger and the temperature of the stream ST at the heat exchanger outlet is less than 250° C., and wherein said hydrocarbon feed comprises long chain paraffins containing 10–14 carbon atoms per molecule which is subjected to dehydrogenation in said at least two reaction zones in the presence of a dehydrogenation catalyst to produce olefins, and said process further comprises alkylating the olefins produced by paraffin dehydrogenation, in the presence of excess benzene, fractionating the effluent from the alkylation step in a distillation column to separate excess benzene from less volatile compounds comprising non transformed paraffins and alkylbenzenes, and using at least a portion of thermal TF from the outlet of said exchanger as a reboiling fluid in said distillation column.

* * * * *

UNITED STATES PATENT AND TRADEMARK OFFICE
CERTIFICATE OF CORRECTION

PATENT NO. : 6,875,338 B2
DATED : April 5, 2005
INVENTOR(S) : Eric Lenglet et al.

It is certified that error appears in the above-identified patent and that said Letters Patent is hereby corrected as shown below:

Title page,
Item [75], Inventors, reads "Lyons (FR)" should read -- Lyon (FR) --.

Column 7,
Line 67, reads "stop is" should read -- step is --.

Column 8,
Line 1, reads "in heat" should read -- in a heat --.
Line 34, reads "claims 10" should read -- claim 10 --.
Line 53, reads "C.520°C." should read -- C-520°C --.
Line 58, reads "benzene" should read -- benzene, --.

Column 9,
Line 8, reads "hydrocarbons" should read -- hydrocarbon --.
Line 10, reads "catalyst at and" should read -- catalyst and --.
Line 11, reads "reheating from the" should read -- reheating the --.
Line 12, reads "from the two" should read -- from the first of the two --.
Line 28, reads "to rebel a" should read -- to reboil a --.

Column 10,
Line 32, reads "A processes" should read -- A process --.

Signed and Sealed this

Nineteenth Day of July, 2005

JON W. DUDAS
*Director of the United States Patent and Trademark Office*